United States Patent
Sasaki et al.

[11] Patent Number: 6,048,546
[45] Date of Patent: Apr. 11, 2000

[54] IMMOBILIZED LIPID-BILAYER MATERIALS

[75] Inventors: Darryl Y. Sasaki; Douglas A. Loy, both of Albuquerque, N.Mex.; Stacey A. Yamanaka, Dallas, Tex.

[73] Assignee: Sandia Corporation, Albuquerque, N.Mex.

[21] Appl. No.: 09/126,686

[22] Filed: Jul. 30, 1998

Related U.S. Application Data

[63] Continuation-in-part of application No. 08/903,980, Jul. 31, 1997, abandoned.

[51] Int. Cl.$^7$ .............................. A61K 9/127; A61K 9/26
[52] U.S. Cl. .................... 424/450; 424/484; 424/486; 428/402.2; 264/4.1; 264/4.3
[58] Field of Search ................................... 424/450, 1.21, 424/9.321, 9.51, 417, 94.3, 484, 486; 436/829; 935/54; 428/402.2; 264/4.1, 4.3

[56] References Cited

U.S. PATENT DOCUMENTS

| | | | |
|---|---|---|---|
| 4,740,375 | 4/1988 | Geho et al. | 424/450 |
| 4,921,757 | 5/1990 | Wheatley et al. | 428/402.2 |
| 5,200,334 | 4/1993 | Dunn et al. | 435/176 |
| 5,300,564 | 4/1994 | Avnir et al. | 5/86 C |
| 5,376,379 | 12/1994 | Fabre et al. | 424/450 |
| 5,616,790 | 4/1997 | Arnold et al. | 562/444 |

FOREIGN PATENT DOCUMENTS

| | | |
|---|---|---|
| 0162724 | 5/1985 | European Pat. Off. . |

OTHER PUBLICATIONS

D. Y. Sasaki, D. R. Shnek, D. W. Pack, and Frances H. Arnold, Metal–Induced Dispersion of Lipid Aggregates: A simple, Selective, and Sensitive Fluorescent Metal Ion Sensor, Chem. Int. Ed. Engl. 1995, 34,905.

D. R. Shnek, D. W. Pack, D. Y. Sasaki, and F. H. Arnold, Specific Protein Attachment to Artificial membranes via Coordination to Lipid–Bound Copper(II), 1994 American Chemical Society.

Lisa M. Ellerby, Clinton R. Nishita, Fumito Nishida, Stacey A. Yamanaka, Bruce Dunn, Joan Selverstone Valentine, Jeffrey I. Zink, Encapsulatin of Proteins in Transparent Porous Silicate Glasses Prepared by the Sol–Gel Method, Reports, Feb. 28, 1992, pp. 1113–1115.

Sabina Merlo and Paul Yager, Optical Method for Monitoring the Concentration of General Anesthetics and Other Small Organic Molecules. An Example of Phase Transition Sensing, 1990 American Chemical Society, vol. 62, pp. 2728–2735.

Smadar Cohen, M. Carmen Bano, Karyn B. Visscher, Marie Chow, Harry R. Allcock, and Robert Langer, Ionically Cross–Linkable Polyphosphazene: A Novel Polymer to Microencapsulation, J. Am. Chem. Soc., 1990, vol. 112, pp. 7832–7883.

(List continued on next page.)

*Primary Examiner*—Gollamudi S. Kishore
*Attorney, Agent, or Firm*—Elmer A. Klavetter

[57] ABSTRACT

A method for preparing encapsulated lipid-bilayer materials in a silica matrix comprising preparing a silica sol, mixing a lipid-bilayer material in the silica sol and allowing the mixture to gel to form the encapsulated lipid-bilayer material. The mild processing conditions allow quantitative entrapment of pre-formed lipid-bilayer materials without modification to the material's spectral characteristics. The method allows for the immobilization of lipid membranes to surfaces. The encapsulated lipid-bilayer materials perform as sensitive optical sensors for the detection of analytes such as heavy metal ions and can be used as drug delivery systems and as separation devices.

30 Claims, 12 Drawing Sheets

OTHER PUBLICATIONS

G. Carturan, R. Campostrini, S. Dire, V. Scardi and E. De Alteriis, Inorganic Gels for Immobilizatin of Biocatalysis: Inclusion of Invertase–active Whole Cells of Yeast (*Saccharomyces cerevisiae*) into Thin Layers of $SiO_2$ Gel Deposited on Glass Sheets, Journal of Molecular Catalysis Letter, 1989, vol. 57, pp. L13–L16.

Anke Reichert, Jon O. Nagy, Wayne Spevak, and Deborah Charych, Polydiacetylen Liposomes Functionalized with Sialic Acid Bind and Colorimetrically Detect Influenza Virus, J. Am. Chem. Soc. 1995, vol. 177, pp. 829–830.

Noga Yerushalmi and Rimona Margalit, Bioadhesive, Collagen–modified Liposomes: Molecular and Cellular Level Studies on the Kinetics of Drug Release and on Binding to Cell Monolayers, Biochem. Biophys. Acta, 1994, vol. 1189, pp. 13–20.

Dana V. Devine, Kenneth Wong, Katherine Serrano, Arcadio Chonn, and Pieter R. Cullis, Liposome–complement Interactions in Rat Serum: Implications for Liposome Survival Studies, Biochim. Biophys. Acta, 1994, vol. 1191, pp. 43–45.

Danilo D. Lasic, Sterically Stabilized Vesicles, Agnew. Chem., Int. Ed. Engl., 1994, vol. 33, pp. 1685–1698.

Hanlan Liu, Shaowei Ong, Louis Glunz, and Charles Pidgeon, Predicting Drug–Membrane Interactions by HPLC: Structural Requirements of Chromatographic Surfaces, Anal. Chem, 1995, vol. 67, pp. 3550–3557.

Joel M. Schnur, Lipid Tubules: A Paradigm for Molecularly Engineered Structures, Science, 1993, vol. 262, pp. 1669–1676.

T. Kunitake, Synthetic Bilayer Membranes: Molecular Design, Self–Organization, and Application, Angew. Chem., Int. Ed. Engl., 1992, 31, 709.

Per Lundahl, Qing Yang, Eva Greijer, and Maria Sandberg, Immobilization of Liposomes in Gel Beads, $2^{nd}$ ed. CRC Press, 1993, vol. 1, 343–61.

Charles Pidgeon and U.V. Venkataram, Immobilized Artificial Membrane Chromatography: Supports Composed of Membrane Lipids, Anal. Biochem., 1989, 176, 36.

R.C. Hresko, I.P. Sugar, Y. Barenholz, and T.E. Thompson, Lateral Distribution of a Pyrene–labeled Phosphatidylcholine in Phosphatidylcholine Bilayers: Fluorescence Phase and Modulation Study, Biochemistry, 1986, 25, 3813–3823.

V. Gabrijelcic and M. Sentjurc, Influence of Hydrogels on Liposome Stability and on the Transport of Liposome Entrapped Substances into the Skin, Int. J. of Pharmaceutics, 1995, 119, 207–212.

C.J. Brinker, K.D., Keefer, D.W. Schaefer, and C.S. Ashley, Sol–gel transition in Simple Silicates, J. Non–Crystalline Solids, 1982, 48, 47–64.

A.L. Weiner, S.S. Carpenter–Green, E.C. Soehngen, R.P. Lenk, and M.C. Popescu, Lipsome–Collagen Gel matrix: A Novel Sustained Drug Delivery System, J. of Pharmaceutical Sciences, 1985, 74(9), 922–925.

PSIDA

PSDSDA

IMMOBILIZED LIPID-BILAYER MATERIALS

This application is a continuation-in-part of U.S. patent application Ser. No. 08/903,980, filed on Jul. 31, 1997, now abandoned.

This invention was made with Government support under Contract No. DE-AC04-94AL85000 awarded by the Department of Energy. The Government has certain rights in the invention.

BACKGROUND OF THE INVENTION

The present invention is directed toward immobilized lipid-bilayer materials and, more particularly, to encapsulated lipid-bilayer materials prepared using a sol-gel method. The encapsulated lipid-bilayer materials are useful in fluorimetric methods for detecting metal ions, as a drug delivery system and in separation science.

Lipid-bilayer materials can perform as sensitive optical sensors for the detection of target analytes, such as heavy metal ions. Lipid-bilayer materials exhibit remarkable response times, selectivity, and easily monitored optical signals. They are also simple in design, inexpensive and easy to fabricate. As free-floating aggregates in solution, detectors utilizing lipid-bilayer materials can be used as simple assay systems (U.S. Pat. No. 5,616,790 issued to Arnold et al. on Apr. 1, 1997). An improvement, however, would be to configure these materials to various solid sensor platforms, offering the advantages of further chemical and physical stabilization of the lipid-bilayer materials and allowing facile handling and the opportunity to recover and reuse them. Still, this effort has been frustrated by the difficulty in immobilizing lipid assemblies to surfaces.

Lipid bilayers are aggregates of lipids held together by hydrophobic interactions that form a variety of different structures, such as closed spherical liposomes (or vesicles), flat discs, globules, tubes, and helices (Kunitake, T. Angew. Chem., Int. Ed. Engl. 1992, 31, 709). Due to their dynamic, self-assembled nature, lipid bilayer assemblies are inherently difficult to fix to solid surfaces. The weak forces that create lipid bilayers are easily disrupted by surface modifications and the lipophilic/hydrophilic balance in the surrounding environment. Surface fixation of liposomes and other lipid-bilayer materials typically results in deformation or lysis of the membrane.

Methods have been developed that overcome some of the difficulties in immobilizing the lipid to a surface without damaging the lipid by using biologically based polysaccharides and biocompatible acrylate gels. For example, entrapped lipid bilayer materials, specifically liposomes, in polysaccharide gels have been used for anesthesia sensors, drug delivery systems, biological studies of membrane proteins and phospholipids, chromatography, and biosensors. However, low liposome entrapment volume, the inability to immobilize pre-formed liposomes, and material instability at elevated temperatures are some of the shortcomings that have not been resolved. Liposome entrapment procedures for these polysaccharide and acrylate gels use both an "in situ entrapment" (Merlo, S.; Yager, P. Anal. Chem. 1990, 62, 2728) which forms the gel around the liposomes and a "pore entrapment" of liposomes in pre-formed gels (Lundahl, P.; Yang, Q.; Greijer, E.; Sandbert, M., Immobilization of Liposomes in Gel Beads; $2^{nd}$ ed.; CRC Press, 1993; Vol. 1, 343–61). The "in situ" procedure calls for elevated temperatures to dissolve the polysaccharides prior to gelation. The liposomes must endure the elevated temperatures during the encapsulation, which means that only thermally stable liposomes can be entrapped. The "pore entrapment" procedure fills large pores in sepharose gels beads with liposomes to be subsequently sealed in the pore. This technique leads to inherent problems with liposome fusion events and poor homogeneous dispersion of liposomes in the matrix, which can lead to problems with sensor and drug delivery applications.

Another difficulty that exists with these organic based immobilization matrices is the potential for biological digestion of the matrix and lipid bilayers by bacteria, fungi, and molds. The organic matrices of collagen gels (Weiner, et al., J. of Pharmaceutical Sciences, 1985, 74, 922), gelatins (Vestar, Europe Patent 0162724), polyacrylates, and DNA (Fabre, P. et. al. U.S. Pat. No. 5,376,379.) materials are ideal hosts for biological growth. In a controlled laboratory environment the gels can be kept in sterilized conditions. However, use of these materials in the natural environment will lead to rapid degradation of the matrix and bilayer assemblies from the infection and colony growth of the biological "predators".

A non-organic gel-type technique has been developed using phosphazene polymers for liposome encapsulation (Cohen, S.; Bano, M. C.; Visscher, K. B.; Chow, M.; Allcock, H. R.; Langer, R., J. Am. Chem. Soc., 1990, 112, 7832). In this procedure, the phosphazene polymer is functionalized with carboxylic acid residues and dispersed in water. Adjustment of the solution pH to 7.5–7.8 generates an ionically cross-linked matrix that can be used to encapsulate bio-materials. A significant drawback to this technique is the narrow pH range of operation beyond which the encapsulation is lost.

Other existing technology can be found in several areas that relate to self-assembled systems in solid materials. Polymerized lipid tubules, formed by aggregation of diacetylenic lipids followed by photopolymerization, have been easily prepared as composite materials with epoxy resins (Schnur, J. M, Science, 1993, 262, 1669). These lipid tubules are, however, polymerized through the diacetylenic functionality that stabilizes the lipid aggregates with strong covalent interactions. Such lipid assemblies are very solvent and temperature durable as is evident in the composite processing which involves acetone suspension of tubules and high temperature/magnetic field material fabrication.

Whole cells have been entrapped in sol-gel materials via similar techniques as described herein, with cellular function maintained (U.S. Pat. No. 5,200,334 issued to Dunn et al. on Apr. 6, 1993; U.S. Pat. No. 5,300,564 issued to Avnir et al. on Apr. 5, 1994; Carturan, C.; Campstrini, R.; Dire, S.; Scardi, V.; DeAlteriis, E., J. Molec. Catalysis, 1989, 57, L13). However, although whole cells consist of membranes similar to liposomes, living cells are inherently robust structures stabilized by membrane imbedded proteins that organize membrane lipids and are supported by a bio-polymer mesh (actin fibers) that gives the cellular membrane structure and stability. Similarly, encapsulation of enzymes and other proteins (Ellerby, et al., Reports, 1992, 1113–1115) is significantly easier to accomplish because of the more robust structures of the proteins. Simple, lipid-only aggregates containing no supporting framework, such as lipid-bilayer materials, are significantly more fragile to immobilization techniques compared to whole cells.

Drug delivery systems based on liposomes have shown promise as drug carriers in animal and human studies (U.S. Pat. No. 4,740,375 issued to Geho et al. issued on Apr. 26, 1988; U.S. Pat. No. 4,921,257 issued to Wheatley et al.

issued on May 1, 1990). However, the liposomes are rapidly removed from the body's blood stream by the spleen and liver as the body recognizes them as foreign invaders. Progress has been made in the circulation time of liposomes in the blood by disguising them with polyethyleneoxide ligands that serve as a "stealth" coating (Lasic, D. D., Angew. Chem., Int. Ed. Engl., 1994, 33, 1685).

Lipid bilayer mimics have recently been used as unique separation materials for peptides, proteins, nucleotides, and oligonucleotides. Lecithin-like molecules were covalently attached to silica particles in an effort to prepare membrane mimics for columns. This support is termed immobilized artificial membranes (IAMs) (Pidgeon, C.; Venkataram, U. V.; Anal. Biochem., 1989, 176, 36). These lecithin-covered column supports could separate biological molecules under milder conditions and with better resolution than conventional chromatographic supports. Furthermore, these supports were very mild to proteins (e.g., cytochrome p450) during separation resulting in no loss of biological activity. Conventional supports often denature the proteins yielding solutions with less than 1 % activity as that prepared from the IAM columns. Materials such as lipid bilayers could also be used as separation materials provided they could be suitably immobilized and fixed to a support.

SUMMARY OF THE INVENTION

The present invention provides a method for encapsulating lipid-bilayer materials by mixing a silica sol with a lipid-bilayer material and allowing the mixture to gel. The sol forms a structure around the lipid-bilayer material that does not covalently bond with the lipid-bilayer material. The sol neither penetrates nor deforms the lipid-bilayer material and the dynamic characteristics of the lipid-bilayer material are maintained indefinitely. The encapsulated lipid-bilayer material has essentially the same fluorescence wavelength and intensity as the lipid-bilayer material has in solution.

The lipid-bilayer materials are selected from a group consisting of liposomes (a spherical lipid-bilayer material), flat disc lipid-bilayer structures, globular lipid-bilayer structures, tubular lipid-bilayer structures, and helical lipid bilayer structures.

The encapsulated lipid-bilayer materials can be easily applied to surfaces and molded into any desirable shape. Such variability in material shape or form will access lipid-bilayer sensor materials to most any sensor platform thereby improving portability, handling, durability, sensitivity and storage time. In addition, the sol-gel material's porous structure can be tailored to desired dimensions. Sol-gel materials can be processed to form monoliths, film/coatings, powders, and fibers. The unique properties of sol-gel materials such as optical transparency, durability, and tailorable properties (e.g. porosity, surface functionalization, thin films, bulk materials) provide an ideal material for sensor applications.

This invention can provide a primary size-selection screening mechanism from the matrix pores for enhanced recognition and sensing of target analytes, such as heavy metals. The invention can additionally be employed as a drug delivery system or a separations system.

The present invention uses an "in situ" approach to attain sol-gel materials with homogeneous dispersion of entrapped lipid bilayers. The ambient temperature at which gel formation takes place and the biologically inert silica matrix allows for a broad range of lipid-bilayer materials to be immobilized in an environmentally stable material. For example, the present invention allows the facile entrapment of liposomes, or lipid bilayers, that are assemblies of non-polymerized, non-covalently interacting lipids.

The present invention differs from the gel technology in several areas. Whereas the above mentioned gels are formed from organic polysaccharides, the present invention uses an inorganic backbone of siloxane bonds to entrap organic lipid-bilayer materials. The inorganic, bilayer-immobilizing matrix is superior to the organic based materials in thermal stability, inhibition of biological pathogen growth, and stability to a wide range of pH. The invention uses aqueous buffered solutions in the sol-gel process making it amenable to development of materials incorporating biological agents. The lipid bilayer/sol-gel material is a unique organic-inorganic composite that is easily formed into various shapes and sizes including monolith blocks and thin films.

The present invention also achieves an alternative to the "stealth" technology by using the sol-gel material as a protective barrier to blood circulating immune systems cells and, more importantly, as an immobilization means to keep the liposomes from entering the liver and spleen. The porous structure of the material will allow the diffusion of target analytes to the liposome surface and subsequently the release of drugs into the bloodstream at a predetermined rate. By eliminating the need for costly and cumbersome "stealth" coatings, the entrapment procedure achieves simpler, cheaper, and better analyte targeted liposomes to be prepared for drug delivery systems. As to bio-compatibility, the silica matrix of these sol-gel materials provides an impervious barrier to microbial attack and enzyme digestion. Their physical stability and porosity (size and volume) are easily tailored through adjustments in gelation conditions and monomer chemistry. Tailoring on this level is difficult with the polysaccharides.

The present invention has several advantages that are an improvement over the IAM column materials. For example, lipid-bilayer materials entrapped in the silica matrix are more biologically similar to cellular membranes than the monolayer of lipids attached to silica of the IAM. This offers a milder and more selective medium for bio-molecule separations. Also, preparation of functionalized liposomes is inherently easier than functionalizing IAMs due to complications in covalent linkage procedures. Thus, a larger selection of functionalized supports result with the liposome entrapped materials. The liposomes can be engineered to act on or respond to particular analytes, much like a sensor system, to facilitate separations. For example, liposomes can respond with a color change as a particular analyte is detected in a mixture. As the analyte travels down the column the color change follows it facilitating sample collection.

BRIEF DESCRIPTIONS OF THE DRAWINGS

The aforementioned objects and advantages of the present invention as well as additional objects and advantages thereof will be more fully understood hereinafter as a result of a detailed description of a preferred embodiment when taken in conjunction with the following drawings in which.

Figure 9:
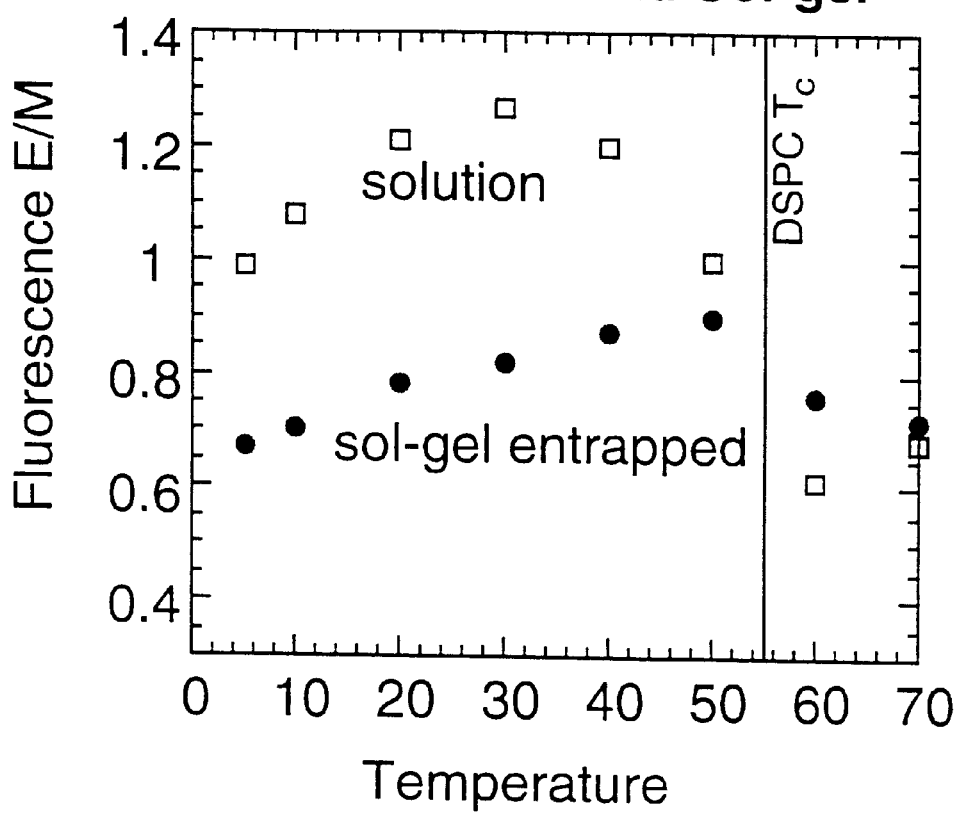

FIG. 9 shows the fluorescence E/M response to temperature for solution phase and sol-gel immobilized 5% PSIDA/DSPC liposomes. From 5–55° C., the solution phase liposome's fluorescence behaves non-ideally while the sol-gel entrapped liposome behaves very near to the ideal. At 55° C., the DSPC transitions from solid phase to liquid phase altering the lipid dynamics subsequently changing the fluorescence E/M.

Figure 10:
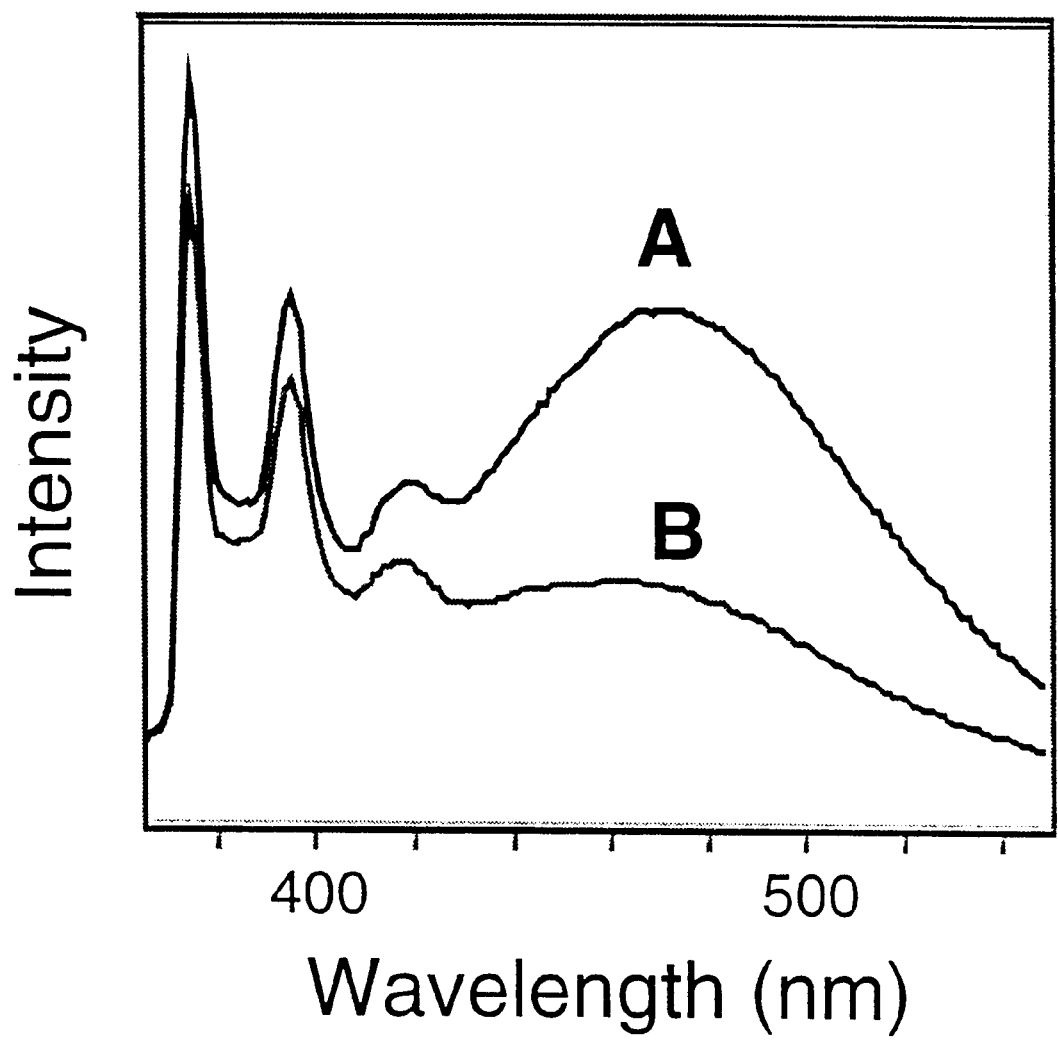

FIG. 10 shows fluorescence spectra of 5% PSIDA/DSPC liposome/sol-gel material in aqueous MOPS buffer solution at pH 7.4 before (A) and after (B) the addition of Mn(II) at 100 $\mu$M concentration.

Figure 11:
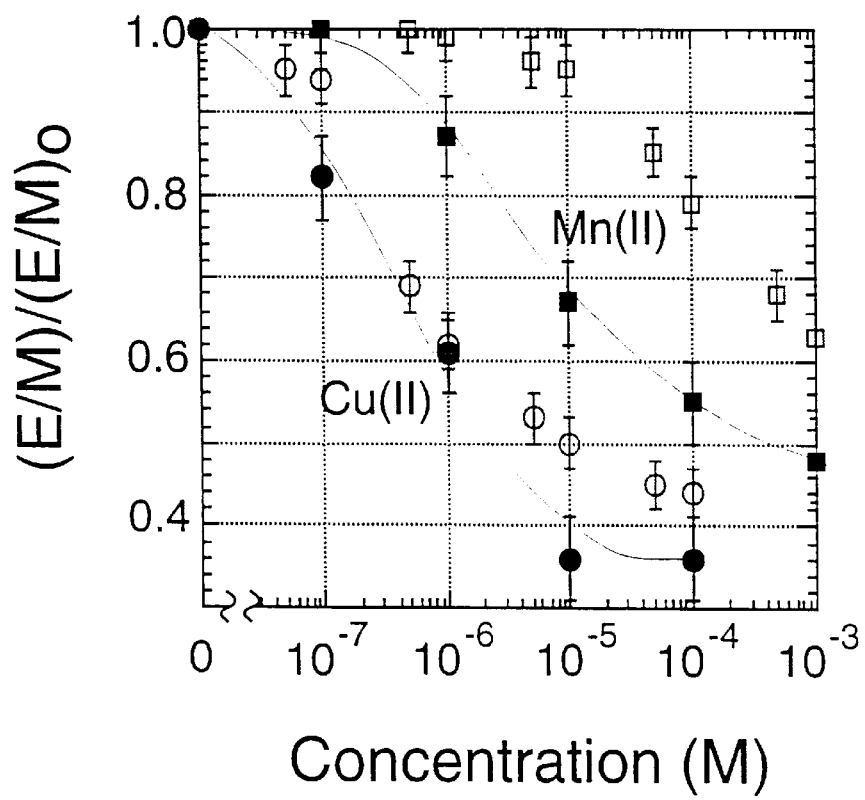

FIG. 11 shows fluorescence metal ion response of 5% PSIDA/DSPC liposomes in solution (open symbols) and as entrapped in TMOS gel (filled symbols) to Cu(II) (circles) and Mn(II) (squares) over a concentration range, demonstrating the enhanced sensitivity of the invention.

Figure 12:
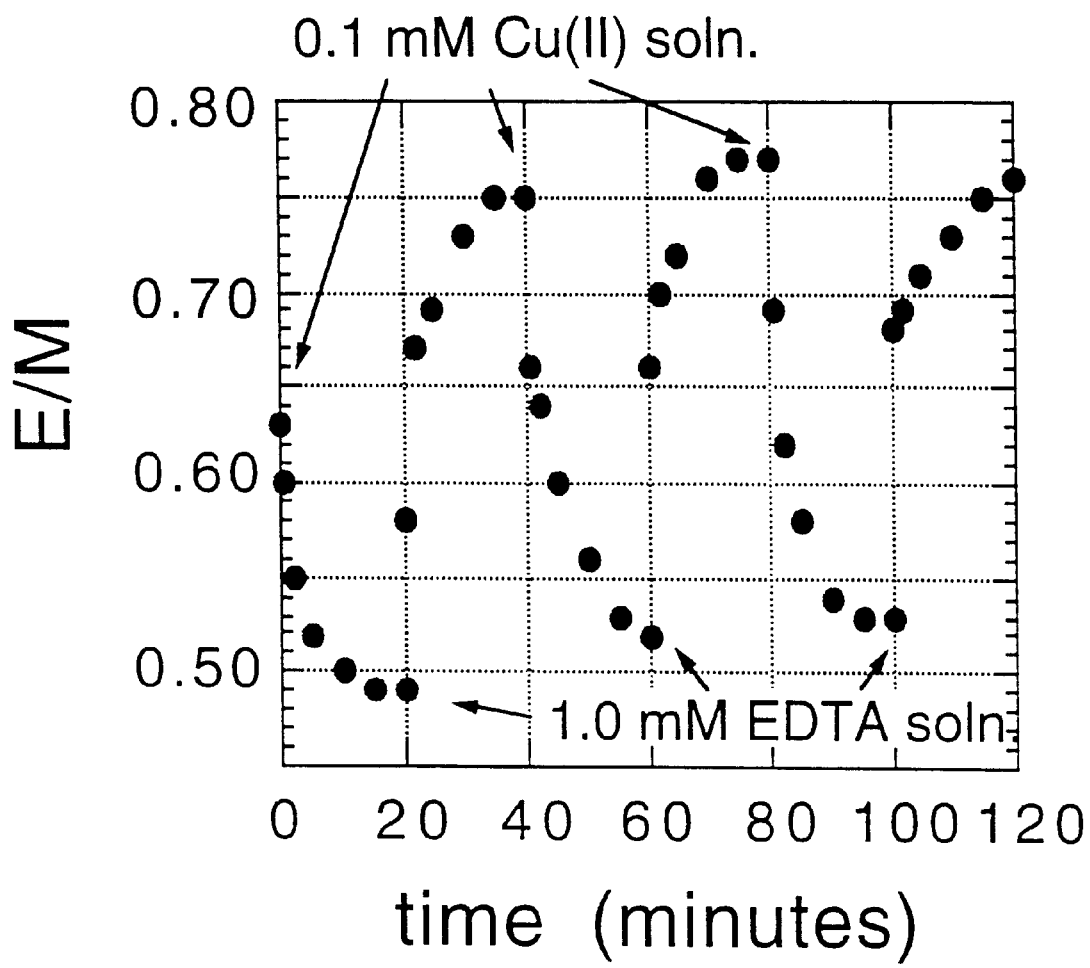

FIG. 12 shows the recycling ability of the sensor material at it responds with decreasing fluorescence excimer to monomer intensity ratio (E/M) to 100 $\mu$M Cu(II) and is regenerated with EDTA at 1000 $\mu$M.

DETAILED DESCRIPTION OF THE INVENTION

In accordance with the present invention, lipid-bilayer materials are immobilized by an entrapment process that gently forms a sol-gel matrix around lipid-bilayer materials in an aqueous environment. A sol is prepared in a standard way (for example, see Brinker, C. J.; Keefer, K. D.; Schaefer, D. W.; Ashley, C. S.; J. Non-Crystalline Solids, 1982, 48, 47, incorporated by reference herein) from an alkoxysilane, preferably tetramethyloxysilane (TMOS) or tetraethyloxysilane (TEOS), and water solution with a small amount of acid or base catalyst. The sol can then be buffered to create desired pH conditions prior to addition of the lipid bilayer material in solution. Following addition of the lipid bilayer solution, the mixture is allowed to gel for a period of time at ambient or near-ambient temperature. During the gel formation, the colloidal sol forms a structure around the lipid-bilayer material (approximately 200–5000 Å diameter) that neither penetrates nor deforms the membrane of the bilayer material. This immobilized lipid-bilayer product can then be formed as a thin film on a surface or used as a solid material for applications such as analyte detection, drug delivery or separations.

An important facet of the present invention is that the immobilization process is sufficiently mild such that no detectable damage of the fragile lipid-bilayer material occurs. Lipid bilayers are an aggregated state of lipid molecules that are held together through weak hydrophobic interactions. Therefore, water plays a vital role to the formation and stability of these aggregate structures. The weak forces that hold the bilayers together make them highly prone to lysis via chemical and physical means. For example, alcohol and other organic solvents and detergents solvate the hydrophobic regions of the membrane, causing the bilayer to rupture and disintegrate. High temperature will also cause the weakly bound membrane lipids to escape the membrane surface resulting in loss of structure. It is quite surprising then that the sol, which contains methanol and large amounts of oligomerized and monomeric alkoxysilanes, does not cause any deterioration of the bilayers as determined by fluorescence measurements. Apparently, the bilayers do not see any chemical or physical difference of the sol from water. As the gel is being formed, the alkoxysilane (e.g., TMOS or TEOS) colloid seems to lack hydrophobic attraction to the midsection of the membrane and are content to form the gel structure surrounding while not invading the membrane. The solvent filled "cavity" of the gel that entraps the bilayer structure, whether a spherical liposome, flat disc, globule, tubular, or helical structured bilayer, appears to mimic the bulk properties of water since the entrapped bilayer structures and their dynamic characteristics are maintained indefinitely.

Figure 1:
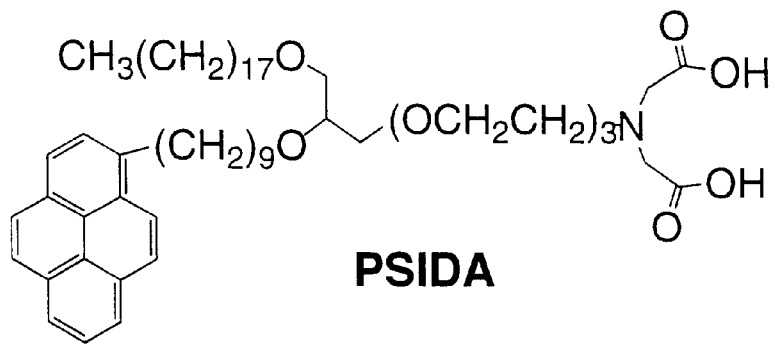
FIG. 1 shows the molecular structures of pyrene-labeled lipids PSIDA and PSDSDA.
Figure 1:
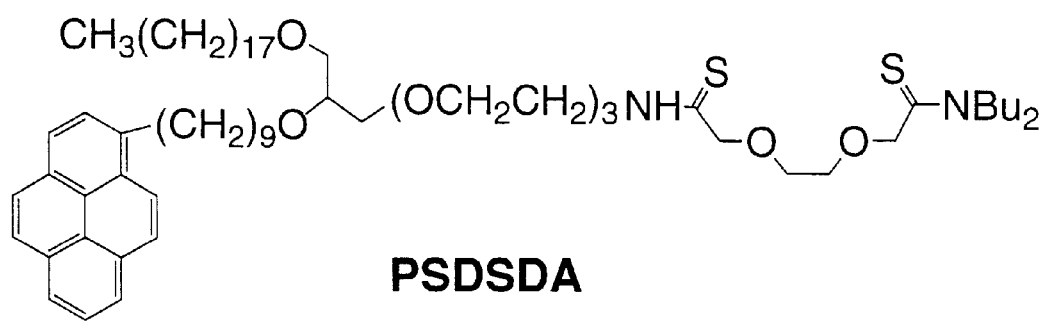
Figure 2:
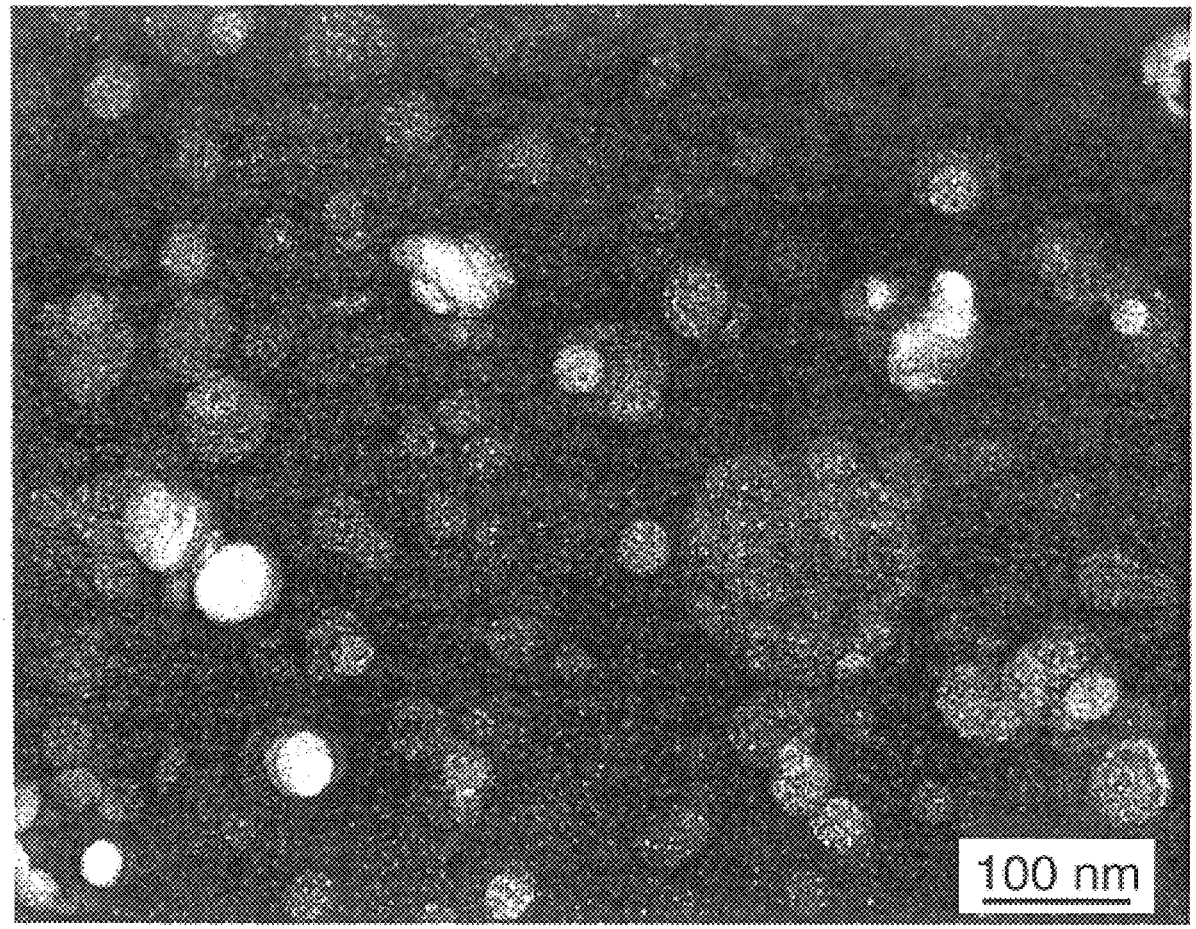
FIG. 2 shows a transmission electron micrograph of 5% PSIDA/DSPC lipid bilayers demonstrating them to be spherical or liposome structures.
Figure 3:
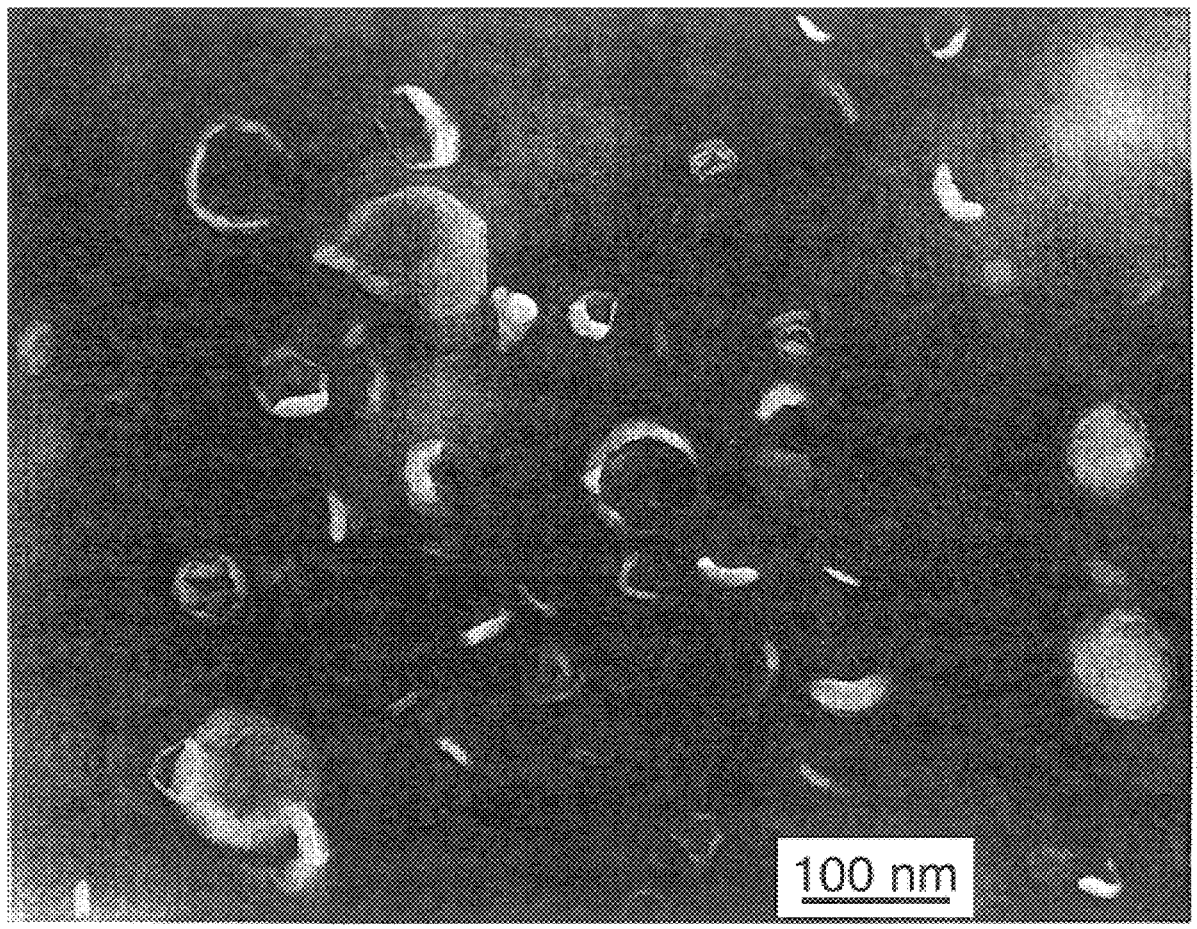
FIG. 3 shows a transmission electron micrograph of 5% PSDSDA/DSPC lipid bilayers showing the bilayer structures to be disc-like, or collapsed bilayers, with some aggregated to larger vesicles.

The encapsulation or entrapping technique is general to immobilize lipid-bilayer materials, where either non-polymerized and polymerized lipid systems can be entrapped. For non-polymer lipid aggregate systems, heavy metal sensitive PSIDA/DSPC and PSDSDA/DSPC fluorescent lipid bilayers were used to demonstrate the method of encapsulation to immobilize the lipid bilayers. The molecular structures of both 1-octadecyl-2-(9-(1-pyrene)nonyl)-rac-glycero-3-(8-(3,6-dioxy)octyl-1-amino-N,N-diacetic acid) [PSIDA] and 1-octadecyl-2-(9-(1-pyrene)nonyl)-rac-glycero-3-(N,N-dibutyl-3,6,12,15-tetraoxa-9-aza-10-thioheptadecylthiamide) [PSDSDA] are shown in FIG. 1. Lipid mixtures of 5% PSIDA or PSDSDA in distearylphosphatidylcholine (DSPC) were prepared as small unilamellar vesicles (SUV), or other lipid assemblies, with mean diameter of approximately 49 nm (approximately 59 nm distribution width), as determined by dynamic light scattering. Transmission electron micrographs of these bilayer assemblies are shown in FIGS. 2 and 3. The 5% PSIDA/DSPC bilayers were generally spherical in structure (liposomes), as seen in FIG. 2, while FIG. 3 shows that the 5% PSDSDA/DSPC bilayers were flat, disc-like assemblies. Both PSIDA/DSPC and PSDSDA/DSPC lipid aggregates were successfully immobilized according to the present invention as is described in more detail in the Examples. In both cases, the bilayers were responsive to specific heavy metal ions with identical fluorescence response as that observed for the free-floating lipids. This means that lipid bilayers of different structures, such as the spherical liposomes and the flat disc lipid bilayers, can be successfully immobilized by encapsulation and be used to detect analytes of interest. Lipid bilayer materials of other structures, such as tubes, globules, and helices, having similar hydrophobic interactions and differing primarily only in geometry, should similarly be able to be immobilized by the encapsulation method of the present invention.

Figure 4:
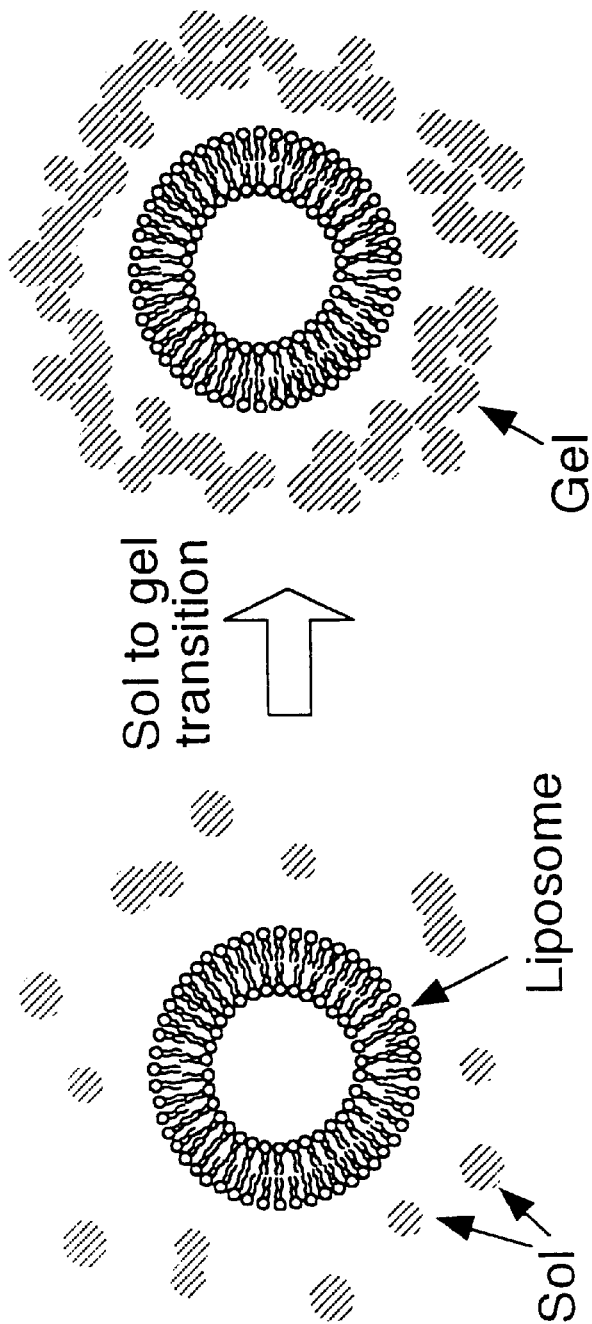
FIG. 4 shows a schematic of the liposome entrapment using the silica sol-gel process of the present invention.

In one embodiment, immobilization of the lipid bilayers in TMOS sol-gels occurred rapidly and quantitatively with no loss of lipid aggregate structure. TMOS sol was prepared by sonicating a heterogeneous solution of TMOS, water, and 0.04 N aqueous hydrochloric acid solution for approximately 20 minutes in a chilled bath until the solution became homogeneous. Solutions of the lipid bilayers at 2 mM concentration in aqueous MOPS buffer solution were cooled in an ice bath along with the TMOS sol. Equal volumes of the sol and lipid solution were mixed together for a half a minute and poured into polystyrene cuvettes to make 5mm× 10mm×18 mm monoliths and onto glass plates with woven mesh to make approximately 193-micron thick thin films. The sol quickly solidified in less than a minute to yield the entrapped lipid bilayers in silica gel (as illustrated in FIG. 4). Gels are typically cured at room temperature for two days before use. The procedure is described in further detail in the Examples.

Figure 5:
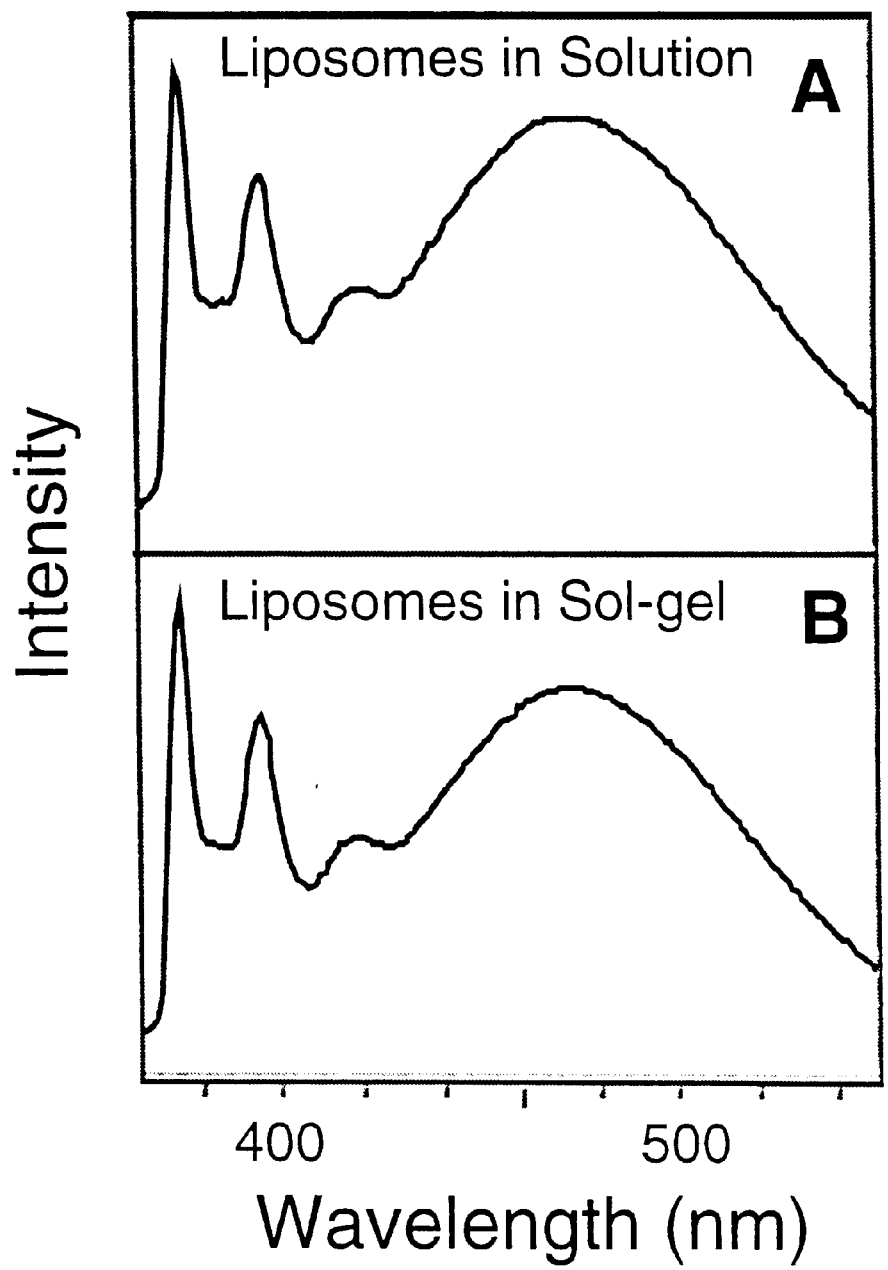
FIG. 5 shows fluorescence spectra of 5% PSIDA/DSPC SUV liposomes in solution (A) and as entrapped in a TMOS sol-gel monolith (B) in accordance with the present invention in aqueous MOPS buffer at pH 7.4 ($\lambda_{ex}$=346 nm).
Figure 6:
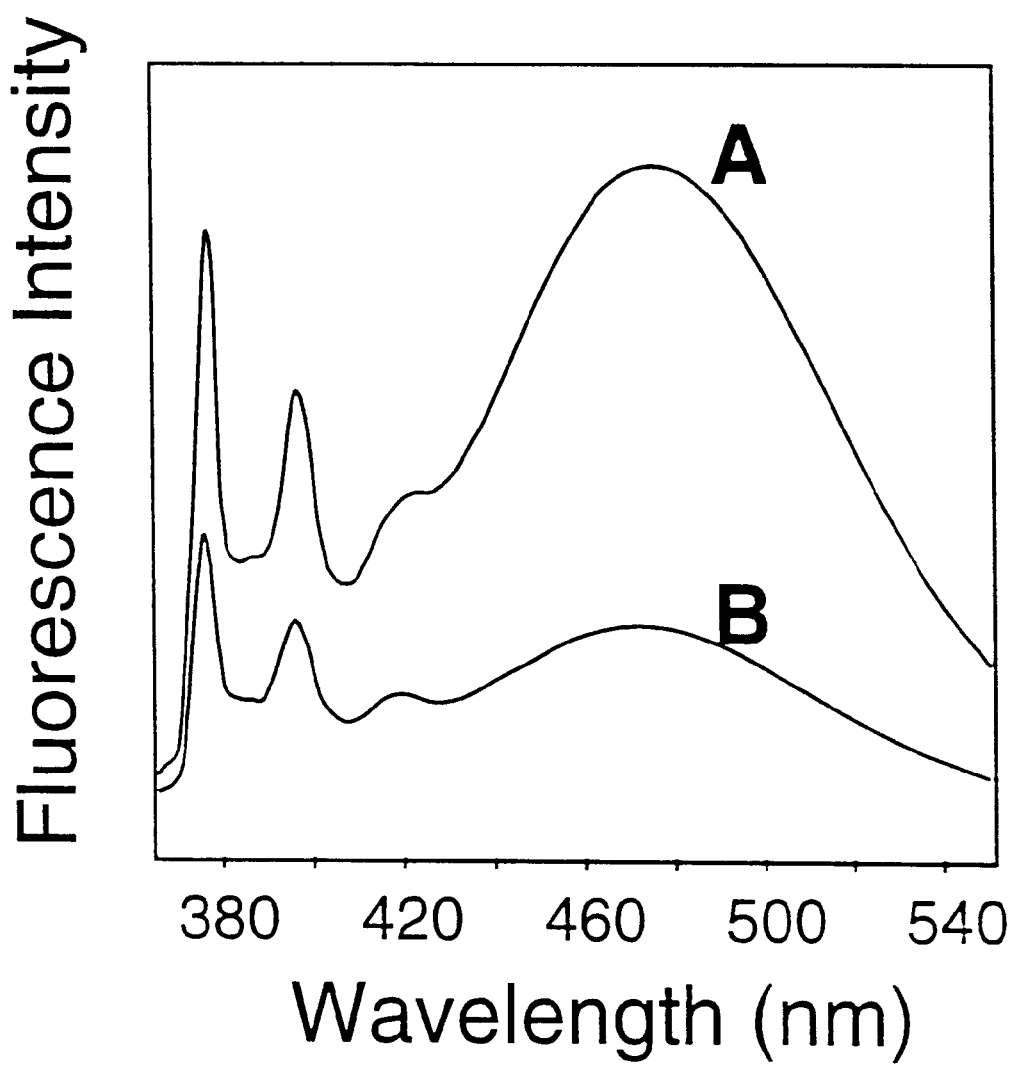
FIG. 6 shows fluorescence spectra of 5% PSIDA/DSPC SUV liposomes entrapped in a TMOS sol-gel monolith in accordance with the present invention before (A) and after (B) soaking 5 days in aqueous MOPS buffer at pH 7.4.

During the sol-gel immobilization process, fluorescence studies of the materials were conducted to examine if the TMOS oligomers and generated methanol from TMOS condensation would have any influence over the structural properties of the lipid bilayer. Excitation of the sol-gel material at 346 nm yields emission maxima at 375 nm for the monomer and at 470 nm from excimer formation of the pyrene fluorophores on the PSIDA and PSDSDA lipid tails. The excimer formation at these lipid concentrations ($5\times10^{-5}$ M) can only occur if the lipids are in an aggregated state. FIG. 5 shows that freely suspended 5% PSIDA/DSPC bilayers in MOPS buffer solution has identical spectral character as that immobilized in TMOS gel. Had the bilayer been disrupted by the sol-gel process resulting in dissolved lipids in solution, the PSIDA lipid would yield only pyrene monomer emission with a maximum emission at 375 nm and no peak at 470 nm. In studies looking at the effect of methanol on the lipid aggregate structure, observable changes in fluorescence intensity and excimer to monomer intensity ratios (E/M) were found at concentrations above 10% methanol/water. The minimal fluorescence changes observed for the entrapped bilayers suggest that the generated methanol from sol-gel processing is lower than 10%. Upon aging of the sol-gel materials in MOPS aqueous buffer solution (pH 7.4), the fluorescence intensity of the liposomes decreases, reaching equilibration after 5 days (FIG. 6). This appears to be due to structural and chemical changes of the silica gel matrix as it equilibrates with the buffer solution.

Figure 7:
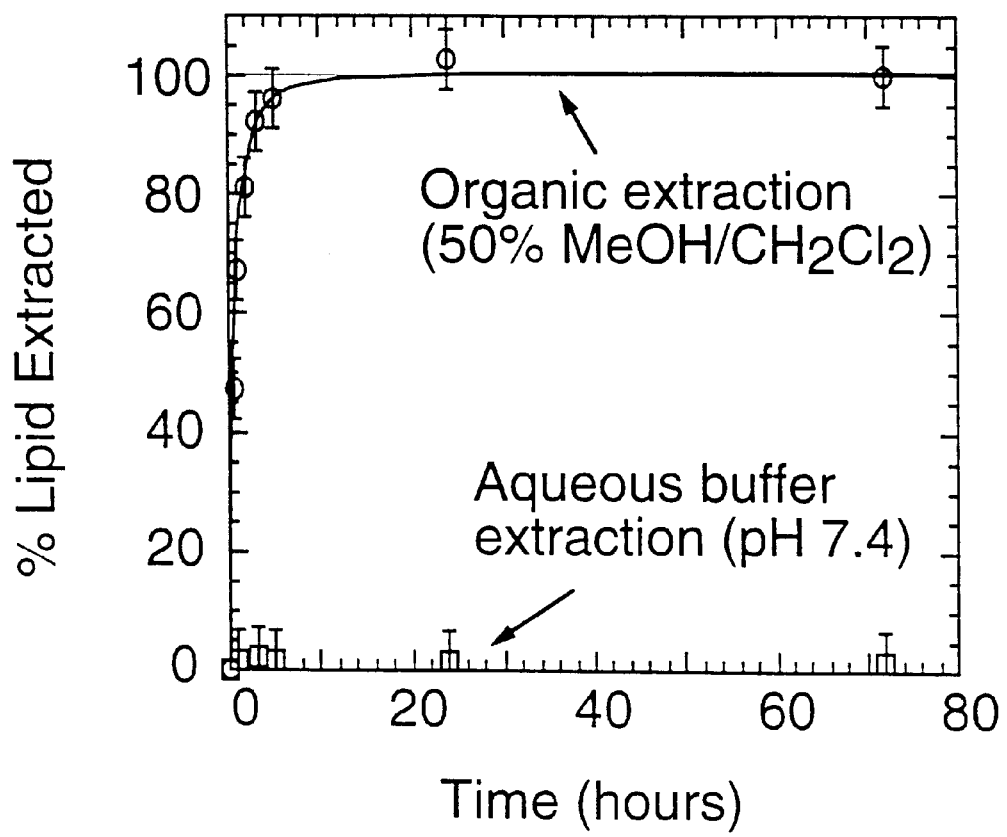
FIG. 7 shows that entrapped PSIDA lipid in accordance with the present invention is quantitatively extracted by 50% methanol/chloroform and is completely immobilized and stable over time in an aqueous solution.
Figure 8:
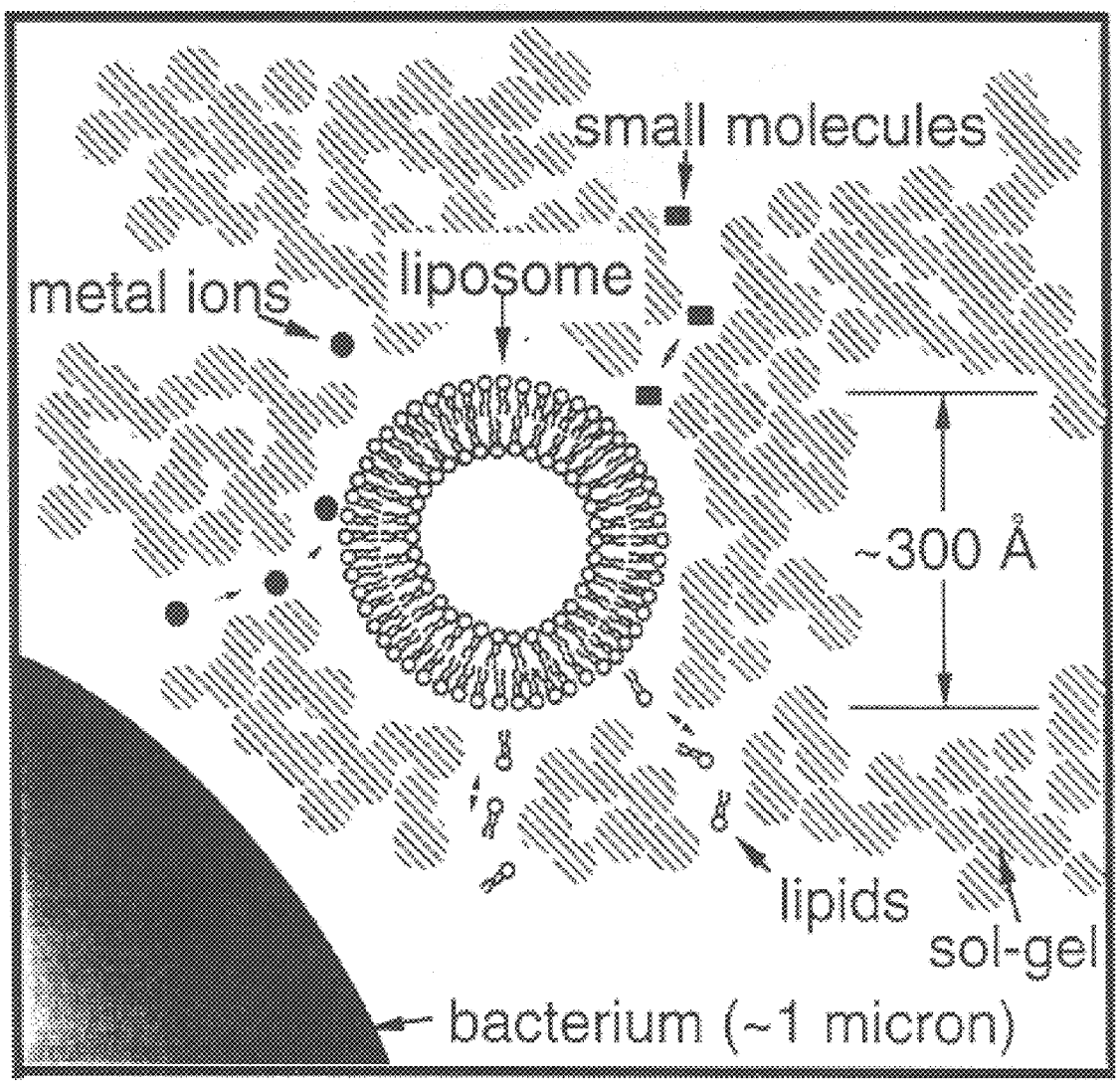
FIG. 8 shows a schematic of an entrapped liposome in a porous sol-gel matrix which allows the permeation of small molecules and ions but inhibits the passage of the liposome to get out to bulk solution while also keeping bacteria out of the material.

The sol-gel procedure results in quantitative entrapment of lipid. Continuous extraction of the sol-gel monolith (18 mm×10 mm×5 mm) containing about 0.4 mM concentration of 5% PSIDA/DSPC lipid in bilayer form at ambient temperature over several months with aqueous buffer fails to liberate any lipid. Extraction with organic solvents (50% methylene chloride/methanol), however, can quantitatively remove all lipids initially immobilized in the sol-gel material within approximately 10 hours as determined by fluorescence measurements using PSIDA lipid as the marker. FIG. 7 shows a plot of lipid removed vs. time that demonstrates that the entrapped liposomes can be dissolved with organic solvent and about 100% of the lipid removed through the porous gel. Once removed, pre-formed liposomes of 5% PSIDA/DSPC cannot be reconstituted into the sol-gel matrix. These results indicate that the lipids are entrapped in the silica gel as large aggregate species (e.g. liposomes) but not covalently attached onto or physically trapped into the gel. Assuming that the initial liposome size does not change during entrapment, the containment "cavities" for the liposomes in the sol-gel material must consist of chambers on the order of 200–5000 Å in diameter connected to smaller diameter channels providing access to the bulk solution. This type of arrangement would allow small molecules, like lipids, to diffuse through the channels but inhibit the diffusion of the larger liposomes (FIG. 8). This characteristic can be useful in drug delivery and separation applications.

Temperature dependent experiments on the lipid bilayer/ TMOS gel materials were conducted to display the stability of these inorganic matrices. Increases in temperature in an ideal lipid bilayer system will produce an increase in translational motion of the molecules within the bilayer enhancing the rate of excimer formation. For the pyrene labeled bilayers described in this invention an increase in E/M with increasing temperature should be observed. Also, if the phase transition temperature of one of the bilayer lipids exists within the experimental temperature range, there will be a shift in E/M reflecting a change in the lipid dynamics at $T=T_c$ (Hresko, R. C.; Sugar, 1. P.; Barenholz, Y.; Thompson, T. E. Biochemistry 1986, 25, 3813). In free bilayer systems in solution such an ideal relationship between E/M and temperature is not always observed due to effects such as bilayer fusion and precipitation from solution. Immobilized liposomes of 5% PSIDA/DSPC according to the present invention, however, exhibit near ideal behavior of E/M vs. T, as is shown in FIG. 9, compared with the free liposomes. The individual lipid bilayer structures appear to be site isolated in the TMOS gel inhibiting fusion events and lipid aggregate precipitation. A linear rise in fluorescence E/M with increasing temperature is observed from 5° C. to 55° C. At 55° C., there is an appreciable drop in E/M correlating with the $T_c$ of DSPC. The E/M vs. temperature profile is reversible even after the material has passed 70° C., with no visible structure changes or deterioration of the gel. Organic matrix materials, such as agarose, acrylamide, sepharose, and DNA dissolve or greatly swell at higher temperatures. These data show the robustness of the present invention at elevated temperatures.

The TMOS gel also offers a protective barrier for the lipid bilayers from biological "predators", such as molds, fungi, and bacteria. Bilayers of 5% PSIDA/DSPC and 5% PSDSDA/DSPC were entrapped in both TMOS silica gels and in agarose gels under similar conditions yielding fluorescent monoliths of dimensions 5 mm×10 mm×18 mm. After just a few days of soaking in fresh MOPS buffer at pH 7.4, the agarose gels were found to have grown internal colonies of bacteria. At the site of the colonies the pyrene fluorescence had disappeared possibly due to the digestion of the bilayers from the growing biologicals. The TMOS materials, however, showed no changes in the monolith's fluorescence visually and spectroscopically even after soaking in the same buffer for several months. The silica matrix is not a good host for the biological "predators" and additionally the pore size of the matrix can be too small for them to penetrate. A scanning electron micrograph picture taken of the lipid bilayer/TMOS sol-gel composite matrix showed that the silica matrix had 20–30 nm diameter pores. Bacteria (>1 micron) and some spores (30–300 nm) would find difficulty in permeating such a material.

The fluorescence properties of the 5% PSIDA/DSPC and 5% PSDSDA/DSPC sol-gel entrapped lipid bilayers can be applied to heavy metal ion sensing as demonstrated in the literature for solution phase systems. It was previously found that divalent metal ion chelation at the iminodiacetic acid headgroup of the PSIDA lipid and dithioamide headgroup of PSDSDA caused initially aggregated pyrene labeled lipid to disperse into the DSPC matrix. The response for heavy metal ions was instantaneous even down to nanomolar concentration levels (i.e., for $Cu^{2+}$ for PSIDA and $Hg^{2+}$ for PSDSDA). The bilayers in the sol-gel composite, likewise, responds to the presence of divalent metal ions with the characteristic fluorescence signal inversion. The fluorescence response of the lipid bilayer/sol-gel material to divalent metal ions can be observed visually for the detection of some metals (e.g., $Cu^{2+}$, $Co^{2+}$, $Hg^{2+}$, $Pb^{2+}$, $Ca^{2+}$ and $Zn^{2+}$) down to micromolar concentration with the green pyrene excimer emission yielding to the bluish emission of the monomer. Equilibration to metal ion in the sol-gel monoliths (18 mm×10 mm×5 mm) is reached within 24 hours, and within 10 min with the 193-micron thick films Soaking of the sol-gel material with entrapped liposomes of 5% PSIDA/DSPC in an aqueous solution of Mn(II) at micromolar concentration causes a change in maximum fluorescence emission from 470 nm and 375 nm (FIG. 10), identical to results reported in the literature for free suspended liposomes.

FIG. 11 shows a plot comparing the fluorescence response $((E/M)/(E/M_O))$ of the 5% PSIDA/DSPC liposomes in a TMOS gel and in solution to selected metal ions, $Cu^{2+}$ and $Mn^{2+}$, over a concentration range. A remarkable result was observed: the liposomes in sol-gel materials exhibited an enhancement in sensitivity for both metal ions over the freely suspended liposomes. This enhanced sensitivity for the sol-gel entrapped liposomes is also observed for other metals, such as $Co^{2+}$, $Cd^{2+}$, $Cr^{2+}$ and $Ni^{2+}$. Dependent on the metal ion, the sensitivity improved by some 4–50 fold. Although the source of this phenomenon is currently unknown these observations are consistent with an anionically charged silicate surface acting as a preconcentrator of divalent metal ions increasing the liposome's local metal concentration. As a confirmation that the observed fluorescence behavior of the PSIDA/DSPC liposome/sol-gel material is not an artifact of heavy metal quenching but rather relies on specific metal binding by the liposomes, additional fluorescence studies with immobilized liposomes of PSOH, a non-metal chelating derivative of PSIDA, at 5% loading with DSPC in sol-gel materials were performed with no response found to heavy metal ion presence at all measured concentration levels.

For sensor applications, the response time and recycling properties of the lipid bilayer/sol-gel composite were also addressed. For the heavy metal sensor, the 5 mm thick gel monoliths and 193-micron thick films were used. The monoliths show response times for complete equilibration, in a stirred solution, ranging from hours with tens of micromolar $Cu^{2+}$ concentrations to days with sub-micromolar concentrations. An observable color change from green to blue with metal ion presence begins at the edges of the monolith and grows inward until the color change is homogeneous throughout. Addition of ethylenediamine tetraacetic acid (EDTA) solution (10 mM) recovers the metal sensor within several hours. The $Cu^{2+}$-EDTA cycle can be conducted several times without any loss of sensor performance (FIG. 12). A clearly distinct response rate difference between $Cu^{2+}$ and EDTA is observed in these studies. The calculated diffusion rate shows at least an order of magnitude faster rate for the doubly anionic, sterically large EDTA ($3\times10^{-7}$ $cm^2$/sec) compared to the doubly cationic $Cu^{2+}$ ($1.5\times10^{-8}$ $cm^2$/sec). Assuming that the response of the liposome to metal and EDTA remains as rapid as in solution (<second) then the difference in response rate can be largely attributed to differences in partitioning of solutes to the surface due to ionic attraction ($M^{2+}$) or repulsion (EDTA) with the anionically charged silicate matrix. The 193-micron thick films, on the other hand, have a response time of approximately 10 minutes for both 0.1 mM Cu(II) and 1.0 mM EDTA with no observable differences between the two response curves.

Immobilization of drug-filled liposomes in silica sol-gels can be used as a controlled drug delivery system as described by Gabrijelcic et al. (Gabrijelcic, V.; Sentjurc, M., Int. J. Pharma., 1995, 118, 207, incorporated by reference herein). Liposomes with entrapped drugs have been used as targeted drug delivery systems. Controlled release of drugs from transdermal patches made of hydrogels filled with drug entrapped liposomes has been a way to administer the drugs in a targeted manner at a constant dosage over time. In a similar way, drug-entrapped lipid bilayers immobilized in a silica sol-gel material can be used as a drug delivery system with the advantages offered by the robust and inert silica matrix. For example, as a transdermal patch, the silica sol's porosity can be tailored to allow the selective permeation of specific analytes for the liposome to respond to. Additionally, the silica surface is inert to biological growth so issues of material sterility or in vivo build up of cellular deposits can be alleviated.

As a separations material, the lipid-bilayer entrapped silica gel can be loaded into liquid phase columns in a similar way to that of Pidgeon et al. (Pidgeon, C.; Venkataram, U. V., Anal. Biochem., 1989, 176, 36, incorporated by reference herein) in their preparation of IAM columns. For the IAM columns, the lipid bilayer is supported on a silica gel bead providing an interface for selective separation of biological material. Silica beads with immobilized lipid-bilayer materials, offer a similar selective support for biomaterials, such as proteins. The added feature of such a material, besides the robust nature of the material with respect to both solution environment and thermal environment, is the tailorable porosity of the silica gel that would provide an added size selectivity for the support.

EXAMPLES

All compounds were of reagent grade purity and used as supplied unless stated otherwise. Organic solvents were of spectral grade from Fisher Scientific. All aqueous solutions were prepared from water purified through a Barnstead Type D4700 NANOpure Analytical Deionization System with ORGANICfree cartridge registering an 18.0 MΩ-cm resistance. Fluorescence spectral data were recorded on a SPEX Fluoromax 2 with Datamax software. All samples were analyzed at 20±0.1° C. using a water jacketed cell. The excitation and emission slits were set at 2 nm bandpass with a scan rate of 0.5 sec/nm.

A. Lipid Extraction From Sol-Gel Monoliths

The experiment was performed by soaking a gel in either 10 mL of MOPS buffer or 50% methanol/chloroform with stirring. A 200 mL aliquot was withdrawn at intervals and placed in a quartz cuvette with a 3.0 mL solution that yielded a resultant solvent mixture of 1:6:6 water/methanol/chloroform. The minimum detection level for PSIDA was 2%. The gels used in the metal studies were equilibrated in MOPS buffer solution (pH 7.4) for 5 days, with an exchange of fresh solution every day, prior to metal exposure. The gels were exposed to divalent metal ion, placing a monolith in a scintillation vial with 7.0 mL of MOPS buffer with the desired metal concentration and the mixture stirred with a drum roller at a 45° tilt until equilibration was reached. The gel was then placed in its original cuvette for analysis.

B. Lipid Bilayer Material Preparation

Stock solutions of distearylphosphatidylcholine (DSPC) and 1-octadecyl-2-(9-(1-pyrene)nonyl)-rac-glycero-3-(8-(3,6-dioxy)octyl-1-amino-N,N-diacetic acid) (PSIDA) and 1-octadecyl-2-(9-(1-pyrene)nonyl)-rac-glycero-3-(N,N-dibutyl-3,6,12,15-tetraoxa-9-aza-10-thioheptadecylthiamide) (PSDSDA) were prepared by dissolving 159 mg of DSPC in 100 mL of chloroform to give a 2.02 mM solution, 5.65 mg of PSIDA in 10 mL of chloroform to give a 0.60 mM solution, and 6.05 mg of PSDSDA in 10 mL of chloroform to give a 0.55 mM solution. From the stock solutions 5.00 mL of DSPC solution and 0.83 mL of PSIDA solution or 0.91 mL of PSDSDA solution were transferred into a 15 mL capacity conical shaped tube. Solvent was removed under reduced pressure on a rotary evaporator at 40–45° C., to form a homogeneously thin lipid film. The films were further dried at room temperature under high vacuum (50 $\mu$mHg) overnight. To the tube was added 3.0 mL of freshly prepared 4-morpholinepropanesulfonic acid (MOPS) buffer solution (0.02 M MOPS, 0.10 M NaCl, pH 7.4). The solution was vortexed at 60–65° C. until the lipid film was completely suspended, degassed with $N_2$ gas for several minutes, then probe tip sonicated on an Ultrasonic Processor at 25 watts at room temperature for ~20 minutes using a cycle of 3 minutes of sonication followed by 3 minutes of resting. The solution was centrifuged for 30 minutes at 16,000 g (Fisher Micro16 Centrifuge) and the supernatant was filtered through a 0.2 mm syringe filter. The clear lipid bilayer solution was then diluted with MOPS buffer to give a desired concentration.

C. Sol-gel Entrapment of Lipid Bilayer, Base Catalyzed—Unbuffered Solution

A sol consisting of a 1:4:4 molar ratio of tetramethoxysilane (TMOS), methanol and water was prepared by mixing 1.475 mL TMOS, 1.620 mL methanol, 0.678 mL aqueous lipid bilayer solution ($10^{-3}$ M total lipid) and 0.072 mL of 0.1 M sodium hydroxide. Other sols have been successfully prepared with other alkoxysilanes (such as tetraethyloxysilane) and with other alcohols. The TMOS sol was stirred for about one hour prior to transferring 0.8 mL aliquots to polystyrene cuvettes. The cuvettes were parafilm sealed and the sol was allowed to gel at room temperature. Upon exposure to UV irradiation (366 nm), the resultant lipid bilayer doped samples did not immediately fluoresce but the characteristic green fluorescence reappeared after the samples were soaked in either 0.01 M MOPS buffer, pH 8 or deionized water.

D. Sol-gel Entrapment of Lipid Bilayer, Acid Catalyzed—Buffered Solution

To prepare a silica sol, a mixture of 15.25 g TMOS, 3.38 g deionized water and 0.22 g of 0.04 N aqueous hydrochloric acid was sonicated in an ice cooled ultrasonic bath for approximately 20 minutes. Neutral pH conditions were then created for the lipid bilayer material in the sol by adding 5 mL of 0.01 M sodium phosphate buffer (pH 7) to 5 mL of the TMOS sol prepared above. To the buffered sol was then added 2.5 mL aqueous lipid bilayer solution ($10^{-3}$ M total lipid). All additions were carried out on ice in order to slow down the sol-gel reactions and thus prevent rapid gelation.

E. Encapsulated Lipid Bilayer Prepared as Gel Monoliths or Thin Films

The encapsulated lipid-bilayer, doped sol of Example D was immediately transferred to polystyrene cuvettes to make 5 mm×10 mm×18 mm gel monoliths or onto a polypropylene mesh, which was then sandwiched between two pieces of polyethylene, to make 200 micron thin films. In the preparation of the thin film gels, it is important to maintain the gel in an aqueous solution to prevent drying and cracking. Gelation generally occurred within a few minutes. The lipid bilayer doped sol-gel samples, as prepared, were fluorescent green when exposed to UV irradiation (366 nm) without further treatment.

F. Heavy Metal Sensing

The lipid bilayer containing sol-gel samples described as Example D above were tested for metal binding by exposure to solutions of the following metals: $Cu^{2+}$, $Mn^{2+}$, $Ca^{2+}$, $Cr^{2+}$, $Cd^{2+}$ and $Pb^{2+}$. Prior to metal exposure, the materials all exhibited the characteristic green fluorescence when exposed to UV irradiation. The gel samples were removed from the cuvettes and allowed to soak in the metal solutions. After soaking in the $Cu^{2+}$, $Mn^{2+}$, $Ca^{2+}$ and $Cr^{2+}$ solutions for up to 24 hours, each of these samples showed a significant decrease in the green fluorescence. The samples soaked in $Cd^{2+}$ and $Pb^{2+}$ on the other hand showed little to no change in the fluorescence. Table 1 summarizes the concentrations of the metal test solutions as well as the excimer to monomer (E/M) ratio for each of the samples.

TABLE 1

| Metal | Solution Concentration | Excimer to Monomer Ratio (E/M) |
|---|---|---|
| $Cu^{2+}$ | $1 \times 10^{-4}$ M | 0.60 |
| $Mn^{2+}$ | $1 \times 10^{-4}$ M | 1.28 |
| $Ca^{2+}$ | $2 \times 10^{-3}$ M | 1.45 |
| $Cr^{2+}$ | $1 \times 10^{-4}$ M | 0.72 |
| $Cd^{2+}$ | $1 \times 10^{-4}$ M | 1.71 |
| $Pb^{2+}$ | $1 \times 10^{-4}$ M | 1.60 |

Note: The E/M for salt water was 1.82.

In addition, the samples prepared by the method described as Example C showed a decrease in the green fluorescence after being exposed to $Cu^{2+}$. Further exposure of the gel sample to 0.1 M EDTA results in the chelation of the $Cu^{2+}$ such that the green fluorescence returns. A similar sample exposed to washes with deionized $H_2O$ did not regain its green fluorescence indicating that the $Cu^{2+}$ did not simply wash out.

The invention being thus described, it will be obvious that the same can be varied in many ways. Such variations are not to be regarded as a departure from the spirit and scope of the invention, and all such modifications as would be obvious to one skilled in the art are intended to be included within the scope of the following claims. All references are incorporated herein by reference.

We claim:

1. A method of preparing an encapsulated lipid-bilayer material, comprising the steps of:
   a) preparing a silica sol;
   b) mixing a lipid-bilayer material in said silica sol; and
   c) allowing said mixture to gel, thereby encapsulating said lipid-bilayer material to form an encapuslated lipid-bilayer material.

2. The method of claim 1, wherein said encapsulated lipid-bilayer materials fluoresce at essentially the same wavelength and intensity as the lipid-bilayer materials in solution.

3. The method of claim 2, wherein said wavelength is approximately 470 nanometers.

4. The method of claim 1, wherein said lipid-bilayer materials are selected from the group consisting of flat disc structures, globular structures, tubular structures, and helical structures.

5. The method of claim 1, wherein said lipid-bilayer materials are non-polymerized liposomes.

6. The method of claim 5, where said non-polymerized liposomes are selected from the group consisting of 1-octadecyl-2-(9-(1-pyrene)nonyl)-rac-glycero-3-(8-(3,6-dioxy)octyl-1-amino-N,N-diacetic acid) and 1-octadecyl-2-(9-(1-pyrene)nonyl)-rac-glycero-3-(N,N-dibutyl-3,6,12,15-tetraoxa-9-aza-10-thioheptadecylthiamide).

7. The method of claim 1, wherein said lipid-bilayer materials are polymerized liposomes.

8. The method of claim 1, wherein said lipid-bilayer materials are flat disc structures.

9. The method of claim 1, wherein said silica sol is buffered to create desired pH conditions prior to addition of said lipid-bilayer material.

10. The method of claim 1, wherein said silica sol is prepared by mixing an alkoxysilane, an alcohol, water, and a base.

11. The method of claim 1, wherein said silica sol is prepared by mixing an alkoxysilane, water, and an acid.

12. The method of claim 1, further comprising the step of removing essentially all lipid-bilayer materials by organic solvents from said silica sol.

13. The method of claim 1, wherein the encapsulated lipid-bilayer material is attached to a surface.

14. The method of claim 1, wherein encapsulated lipid-bilayer material forms a chamber of greater than about 200 Angstroms in diameter.

15. The method of claim 1, wherein said encapsulated lipid-bilayer material forms a chamber of less than about 5000 Angstroms in diameter.

16. The method of claim 13, employing the encapsulated lipid-bilayer material attached to a surface as a sensor to sense the presence of heavy metals, further comprising the steps of:
  a) exposing said encapsulated lipid-bilayer material attached to a surface to UV irradiation to obtain a baseline fluorescence;
  b) exposing said encapsulated lipid-bilayer material attached to a surface to a solution containing one or more heavy metals for up to 24 hours;
  c) exposing said encapsulated lipid-bilayer material attached to a surface to UV irradiation to detect a change in fluorescence, thereby indicating the presence of a heavy metal.

17. The method of claim 16, wherein said one or more heavy metals are selected from the group consisting of copper, cobalt, cadmium, chromium, nickel, manganese, lead, zinc, mercury, and calcium.

18. The method of claim 1, wherein said encapsulation occurs at temperatures in about the range of approximately 0° C. to approximately 70° C.

19. The method of claim 1, wherein the lipid-bilayer materials do not form covalent bonds with the sol-gel matrix.

20. The method of claim 1, further comprising the step of preparing the encapsulated lipid-bilayer materials as a thin film.

21. The method of claim 1, further comprising the step of employing the encapsulated lipid-bilayer materials as a drug delivery system.

22. The method of claim 1, further comprising the step of employing the encapsulated lipid-bilayer materials as a means to separate biological molecules.

23. An encapsulated lipid-bilayer material manufactured according to the method of claim 1.

24. A process for encapsulating a lipid-bilayer material, which comprising the steps of:
  a) preparing a silica sol from an alkoxysilane and water solution with a small amount of acid or base catalyst;
  b) adding a buffering agent;
  c) mixing said lipid-bilayer material in said silica sol; and
  d) allowing said mixture to gel, thereby encapsulating the material.

25. The method of claim 24, further comprising the step of preparing the encapsulated lipid-bilayer materials as a thin film.

26. The method of claim 24, further comprising the step of employing the encapsulated lipid-bilayer material as a sensor to sense the presence of heavy metals.

27. The method of claim 24, further comprising the step of employing the encapsulated lipid-bilayer materials as a drug delivery system.

28. The method of claim 24, further comprising the step of employing the encapsulated lipid-bilayer materials as a means to separate biological molecules.

29. A method of preparation of an encapsulated lipid-bilayer material, comprising the steps of:
  a) preparing a silica sol by mixing tetramethoxysilane, water and hydrochloric acid solution to from a homogeneous sol solution;
  b) adding a lipid-bilayer solution to said homogeneous sol solution;
  c) allowing said mixture to gel, thereby encapsulating said lipid-bilayer material to form an encapsulated lipid-bilayer material.

30. The method of claim 4, wherein the globular structures are liposomes.

* * * * *